United States Patent [19]

Pozzo

[11] Patent Number: 5,113,008
[45] Date of Patent: May 12, 1992

[54] PROCESS FOR PRODUCING HEMIKETALS AND HEMITHIOKETALS

[75] Inventor: Mark J. Pozzo, St. Louis, Mo.

[73] Assignee: Monsanto Company, St. Louis, Mo.

[21] Appl. No.: 643,294

[22] Filed: Jan. 22, 1991

[51] Int. Cl.$^5$ ................... C07C 327/00; C07C 69/66
[52] U.S. Cl. ................................ 558/252; 560/184
[58] Field of Search ............... 558/252, 251; 549/417; 560/184

[56] References Cited

U.S. PATENT DOCUMENTS

| 4,618,679 | 10/1986 | Lee | 549/417 |
| 4,647,689 | 3/1987 | Micinski | 560/174 |
| 4,785,129 | 11/1988 | Goure | 558/253 |

FOREIGN PATENT DOCUMENTS 931689  7/1963  United Kingdom ............... 560/174

Primary Examiner—Mary C. Lee
Assistant Examiner—Robert C. Whittenbaugh
Attorney, Agent, or Firm—Grace L. Bonner; Stanley M. Tarter; Howard C. Stanley

[57] ABSTRACT

Hemiketals and hemithioketals are produced by bringing into reactive contact an alcohol or mercaptan and an oxetan-2-one compound having the following structural formula:

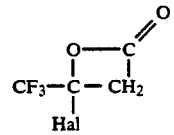

where Hal is a halogen.

18 Claims, No Drawings

PROCESS FOR PRODUCING HEMIKETALS AND HEMITHIOKETALS

BACKGROUND OF THE INVENTION

The present invention relates to a new and useful process for producing hemiketals and hemithioketals. More particularly, the present invention relates to a process for producing certain hemiketals and hemithioketals useful in manufacturing alkyl 4,4,4-trifluoroacetoacetate or thioalkyl 4,4,4-trifluoroacetoacetate.

As part of their chemical structure, many agriculturally and pharmaceutically active compounds contain at least one trifluoromethyl functional group. The presence of one or more such groups in the compounds contributes to the desired activity of the compounds. In U.S. Pat. No. 4,785,129, compounds of alkyl 4,4,4-trifluoro-3-oxo-butanethioates, which are also referred to as thioalkyl trifluoroacetoacetates, are disclosed, along with the fact that methyl and ethyl esters of 4,4,4-trifluoro-3-oxo-butanoic acids are commercially available compounds. It is also disclosed in that patent that such compounds are useful intermediates for the preparation of herbicidal pyridine dicarbothioates and herbicidal pyridine dicarboxylates.

In U.S. Pat. No. 4,618,679, the preparation of herbicides using a 3-ketoester and suitable aldehydes as intermediates is disclosed.

Various processes for making trifluoroacetoacetic acid compounds are known. For example, U.K. specification No. 931,689 discloses the manufacture of fluorinated acetoacetic acid chlorides, wherein a fluorinated acetyl chloride is reacted with ketene, desirably in the presence of a suitable solvent.

SUMMARY OF THE INVENTION

The present invention provides a new and useful process for making hemiketals and hemithioketals.

The process for producing the hemiketals or hemithioketals involves bringing into reactive contact an alcohol or mercaptan and an oxetan-2-one compound having the following formula:

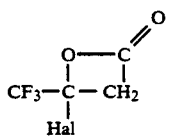

wherein Hal is a halogen to produce a hemiketal or hemithioketal having the structural formula:

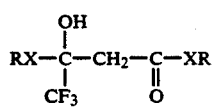

where X is O or S and R is a lower alkyl, i.e., $C_1$-$C_{12}$ alkyl. For best yields the mercaptan or alcohol is used in near or above stoichiometric amounts. Where mercaptan is used as a reactant, it is preferred that the reaction be carried out in the presence of a catalytic amount of a tertiary amine. The preferred source of the oxetan-2-one compound is a recovered by-product resulting from the manufacture of fluorinated acetoacetic acid chloride using a process, such as that disclosed in the above-mentioned U.K. specification.

DETAILED DESCRIPTION OF THE INVENTION

As used herein, the term "lower alkyl" and cognates thereof, such as, "alk" etc., refers to an alkyl moiety, straight or branched chain, having from 1 to about 12 carbon atoms.

In a known process, ketene is reacted with trifluoroacetyl halide, preferably trifluoroacetyl chloride, in a solvent and at a reduced temperature to produce trifluoroacetoacetyl halide. The following equation depicts the reaction:

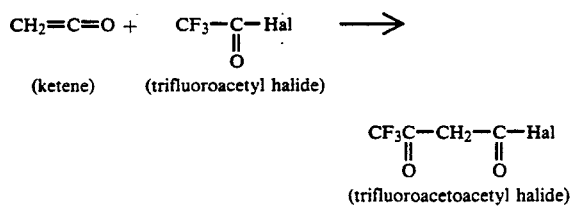

wherein Hal is a halogen, such as Cl, Br or F. Also, produced in substantial quantities in amounts of about 10% by weight in the reaction between ketene and a trifluoroacetyl halide is a 4-halo-4-trifluoromethyl-oxetan-2-one compound having the following structural formula:

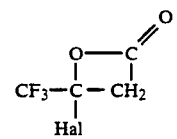

wherein Hal is a halogen, such as Cl, Br, or F. After quenching with either a lower alcohol or mercaptan, the reaction mixture can be distilled to separate the Oxetan-2-one compound, solvent and trifluoroacetoacetate compound one from the other. Preferably, the distillation is carried out at a reduced pressure to minimize the production of unwanted by-products.

The oxetan-2-one compound that is recovered from the distillation operation is converted to a hemiketal or hemithioketal by reacting the same with excess lower alkyl monohydric alcohol or mercaptan, respectively. For best results, the mol ratio of alcohol or mercaptan to oxetan-2-one compound is in the order of about 5:1 to 1:1. A preferred ratio is 3.5:1 to 2.5:1. The mixture can be heated at reflux to convert the oxetan-2-one compound into a hemiketal or hemithioketal in accordance with the following illustrative equation:

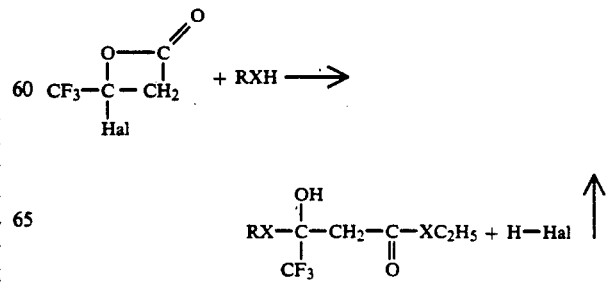

where X, R and Hal are as defined above.

The resulting product is 4,4,4-trifluoro-3-ethoxy-3-hydroxy-butanoic acid, ethyl ester, where ethanol is used as a reactant or is 4,4,4-trifluoro-3-thiomethyl-3-hydroxy-butanoic acid, methylthioester where methyl mercaptan is used as a reactant.

Preferably, the hemiketal or hemithioketal is converted to alkyl or S-alkyl trifluoroacetoacetate. This can be accomplished by stripping off excess alcohol or mercaptan from the reaction mixture and, at the same time, cleaving off the alkoxy or thioalkyl radical from the hemiketal in the form of an alcohol or mercaptan. The stripping and cleaving are carried out preferably at atmospheric pressure at a reflux ratio of 10:1 to 1:1, most preferably about 5:1. The operation is preferably done at or near atmospheric pressure because temperatures above about 90° C. are needed to crack the hemiketal to the desired alkyl or S-alkyl 4,4,4-trifluoroacetoacetate. The trifluoroacetoacetate resulting from the conversion of the hemiketal or hemithioketal can be combined with the trifluoroacetoacetate resulting from the reaction wherein the oxetan-2-one compound is produced as a by-product and thereafter used in the preparation of herbicidal pyridine compounds. Thus, a product previously regarded as a waste product in the manufacturing of trifluorinated acetoacetic compounds from a fluorinated acetyl halide and ketene is converted to a product useful in preparing additional quantities of trifluoroacetoacetate, thereby increasing significantly the overall yield of trifluoroacetoacetate by about 5-10%.

It has been found that the conversion of oxetan-2-one compound to a thioate for best results should be carried out in the presence of a catalytic amount of a tertiary amine, such as triethylamine. A catalytic amount may range from about 5-30% of the weight of mercaptan employed. The mol ratio of oxetan-2-one compound to amine can range from about 1.5:1 to 0.5:1. Examples of tertiary amines useful in the promotion of the reaction between the oxetan-2-one compound and mercaptan include trimethylamine, triethylamine, tributylamine, tri-t-butylamine, N,N-diisopropylethylamine, 4-dimethyl-aminopyridine, 1,8-diazabicyclo(5.4.0)undec-7-ene, 1,5-diazabicyclo(4.3.0)non-5-ene, 1,4-diazabicyclo(2.2.2)octane.

The following examples are given to more particularly illustrate the invention and the invention is not to be regarded as being limited thereto. All parts are given on a weight basis unless otherwise indicated.

EXAMPLE 1

Three parts of absolute ethanol and 1 part of 4-chloro-4-trifluoromethyl-oxetan-2-one contained in the low boiling distillate of the reaction product of ketene and fluorinated acetoacetic acid chloride were mixed together and heated at reflux at a temperature of about 100° C. for one hour. It was determined that the reaction product comprised about 40% by weight 4,4,4-trifluoro3-ethoxy-3-hydroxy-butanoic acid, ethyl ester.

EXAMPLE 2

Three parts of methyl mercaptan, 1 part of 4-chloro-4-trifluoromethyl-oxetan-2-one contained in the low boiling distillate of the reaction product of ketene and fluorinated acetoacetic acid chloride, and 0.2 part of triethylamine were heated at reflux at a temperature of about 100° C. for one hour. It was determined that the reaction product comprised about 40% by weight 4,4,4-trifluoro-3-ethoxy-3-hydroxy-butanoic acid, methylthioate.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and description set forth hereinabove but rather that the claims be construed as encompassing all the features of patentable novelty which reside in the present invention, including all features which would be treated as equivalents thereof by those skilled in the art to which the invention pertains.

What is claimed is:

1. A process for producing a hemiketal comprising bringing into reactive contact an oxetan-2-one compound having the formula:

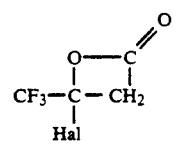

wherein Hal is a halogen with an alcohol to produce a hemiketal having the formula:

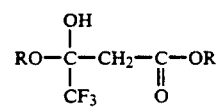

wherein R is a lower alkyl radical.

2. The process of claim 1 wherein the alcohol is present in near or above stoichiometric amount.

3. The process of claim 2 wherein the alcohol and oxetane-2-one compound are heated at reflux to produce the hemiketal.

4. The process of claim 2 wherein the mol ratio of alcohol to oxetane-2-one compound is in the order of about 5:1 to 1.5:1.

5. The process of claim 3 wherein the mol ratio is from 3.5:1 to 2.5:1.

6. The process of claim 1 wherein the alcohol is ethanol.

7. The process of claim 2 wherein the alcohol is ethanol.

8. The process of claim 3 wherein the alcohol is ethanol.

9. A process for producing a hemithioketal comprising bringing into reactive contact in the presence of a catalytic amount of a tertiary amine an oxetan-2-one compound having the formula:

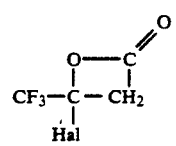

wherein Hal is a halogen with a mercaptan to produce a hemithioketal having the formula:

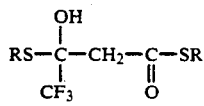

wherein R is a lower alkyl radical.

10. The process of claim 9 wherein the mercaptan is present in near or above stoichiometric amount.

11. The process of claim 10 wherein the mercaptan and oxetan-2-one compound are heated at reflux to produce the hemithioketal.

12. The process of claim 9 wherein the mol ratio of mercaptan to oxetan-2-one compound is in the order of about 5:1 to 1.5:1.

13. The process of claim 2 wherein the mol ratio of mercaptan to oxetane-2-one compound is in the order of about 3.5:1 to 2.5:1.

14. The process of claim 9 wherein the mercaptan is methyl mercaptan.

15. The process of claim 10 wherein the mercaptan is methyl mercaptan.

16. The process of claim 11 wherein the mercaptan is methyl mercaptan.

17. The process of claim 1 wherein the halogen is chlorine.

18. The process of claim 9 wherein the halogen is chlorine.

UNITED STATES PATENT AND TRADEMARK OFFICE
CERTIFICATE OF CORRECTION

PATENT NO. : 5,113,008

DATED : May 12, 1992

INVENTOR(S) : Mark J. Pozzo

It is certified that error appears in the above-identified patent and that said Letters Patent is hereby corrected as shown below:

Column 6, line 5, (claim 13) "The process of claim 2 wherein" should read --The process of claim 12, wherein--.

Signed and Sealed this

Twenty-eighth Day of September, 1993

*Attest:*

BRUCE LEHMAN

*Attesting Officer*         *Commissioner of Patents and Trademarks*